United States Patent [19]

Nawrocki

[11] Patent Number: 5,670,175
[45] Date of Patent: Sep. 23, 1997

[54] PROCESS FOR OBTAINING ULTRAPURE EGG OIL AND ITS USE

[76] Inventor: Werner C. Nawrocki, Landvogtstrasse 4, Frankfurt am Main, D-60320, Germany

[21] Appl. No.: 530,349
[22] PCT Filed: Feb. 20, 1995
[86] PCT No.: PCT/EP95/00609
  § 371 Date: Sep. 27, 1995
  § 102(e) Date: Sep. 27, 1995
[87] PCT Pub. No.: WO95/22590
  PCT Pub. Date: Aug. 24, 1995

[30] Foreign Application Priority Data

Feb. 21, 1994 [DE] Germany .......... 44 05 486.6

[51] Int. Cl.$^6$ .......... A61K 35/54
[52] U.S. Cl. .......... 424/581; 424/DIG. 13; 426/601; 426/641; 426/425; 426/492
[58] Field of Search .......... 424/581, DIG. 13; 426/601, 641, 425, 492

[56] References Cited

U.S. PATENT DOCUMENTS

| | | | |
|---|---|---|---|
| 4,219,544 | 8/1980 | Burg | 424/581 |
| 4,219,585 | 8/1980 | Herring | 426/614 |
| 5,028,449 | 7/1991 | Hatanaka | 426/614 |

FOREIGN PATENT DOCUMENTS

| | | |
|---|---|---|
| 4200678 | 7/1992 | Germany . |
| 2072016 | 9/1981 | United Kingdom . |

OTHER PUBLICATIONS

Database WPI—Abstract 92–364471 (1992).
Database WPI—Abstract 91–199441 (1991).
Database WPI—Abstract 91–004849 (1991).
Database WPI—Abstract 85–113564 (1985).
Pat. Abs. Japan 14(456) (1990)—Japanese 2180994.
Melnick, Cos. Perf., 88(1): 31–37 (1973).

*Primary Examiner*—Jean C. Witz
*Attorney, Agent, or Firm*—Graham & James LLP

[57] ABSTRACT

An ultrapure egg oil is prepared starting from dried and powdered avian or reptilian egg yolk by means of extraction with the aid of fat solvents, followed by two-step ageing, first at ambient temperature and then at a lowered temperature, separating off and centrifuging off the less viscous phase formed and again separating off the less viscous component. This component is, if appropriate repeatedly, mixed with demineralized water and heated, and, after cooling, the less viscous phase is separated off and again centrifuged, the less viscous component is again separated off and held at a lower temperature, the phases are again separated, and the less viscous component which has been separated off is recentrifuged.

This again results in phase separation, the less viscous component which has been separated off being the end product which is a yellow to reddish, fluid oil which can be stored without preservatives.

The ultrapure egg oil prepared by this process can be used for the treatment of skin burns, including sunburn, and for regenerating the skin in cosmetic products.

23 Claims, No Drawings

PROCESS FOR OBTAINING ULTRAPURE EGG OIL AND ITS USE

A substantial disadvantage shared by the many customary pharmaceuticals for the treatment of skin burns, in particular sunburn, which are prepared on an industrial scale by the prior art is that the active substances used lack stability to decomposition. The same applies to a large number of commercially available cosmetic preparations for skin regeneration. As a rule, this results in the necessity of having to add to these products preservatives during the production process which facilitate long-term storage of the product, or even make it possible in the first place. However, the fact that such preserving additives have potential side effects which are difficult to estimate and can frequently not be fully delimited or even predicted, is frequently a decidedly undesirable risk factor for the user of the pharmaceuticals. Bearing in mind that there is an increasing occurrence of civilizational skin disorders, in particular a striking increase in the occurrence of all sorts of skin allergies, it is desirable to effectively delimit or, as far as possible, to fully eliminate the spectrum of potential health hazards presented by preserving additives in pharmaceuticals of the type mentioned at the outset.

The present invention describes a process for the preparation of an ultrapure egg oil which can be obtained from avian or reptilian egg yolk. Being natural, the product can be employed for the therapy of all sorts of skin burns, including sunburn, and also as an active substance for regenerating diseased areas of the skin, or areas of the skin which are affected due to particular stress. In this context, it must be stressed that the invention, which involves a multi-step purification process, eventually leads to an ultrapure product which allows any preserving additives for improving storage stability to be dispensed with completely. Since the product does not depend on stabilizing preservatives, it is possible to completely rule out all the above-described side effects and health hazards.

The process according to the invention comprises a specific combination of process steps, the aim of obtaining an ultrapure egg oil only being achieved by their totality and the sequence indicated. Accordingly, the process is characterized by the following process steps:

a) drying the egg yolk at temperatures up to 90° C. and comminuting the dried egg yolk to give a pulverulent product (A), b) extracting the product (A) obtained in step (a) over a period of three to seven days using a fat-dissolving extractant, c) slowly distilling off the extractant to obtain a viscous residue (B), d) ageing the residue (B) obtained in step (c) at ambient temperature over a period of up to 10 hours, preferably for five to seven hours, e) further ageing the residue (B) at a temperature of between 7° and 12° C. over a period of up to 24 hours until distinct phase separation takes place, f) separating off the less viscous phase (C) formed upon phase separation in step (e), g) centrifuging the less viscous product (C) obtained in step (f) for 20 to 40 minutes at a speed of up to 7,000 revolutions per minute, and separating off the less viscous phase (D), h) mixing the product (D) obtained in step (g) with demineralized water in a ratio of 1:2 to 1:5 by volume, and heating the mixture over a period of 30 to 90 minutes at a temperature of 90° to 120° C., preferably 95° to 100° C., i) cooling the aqueous mixture obtained in step (h) to ambient temperature, and separating off the less viscous component (E), j) centrifuging the product (E) obtained in step (i) for 20 to 40 minutes at a speed of up to 7,000 revolutions per minute, and separating off the less viscous phase (F), k) holding the product (F) obtained in step (j) at temperatures from 7° to 12° C. over a period of up to 24 hours until distinct phase separation takes place, and separating off the less viscous phase (G), l) centrifuging the product (G) obtained in step (k) for 20 to 40 minutes at a speed of up to 7,000 revolutions per minute, and separating off the less viscous phase (H), m) if appropriate, repeating the measures of steps (h) to (l) or (j) to (l) using the product (H) obtained in step (l).

The starting material employed in the process of the present invention is the egg yolk of birds, such as chickens, ducks, ostriches and the like, or, alternatively, of reptiles, such as, for example, turtles. This starting material is dried in a first process step (a) at temperatures of not more than 90° C., preferably between 50° C. and 70° C. On an industrial scale, dried egg yolk is, as a rule, prepared in a so-called falling-film tower; alternatively, drying ovens, for example those operating with circulating air, are also suitable. The dried egg yolk is comminuted to a mean particle size of between, for example, 0.3 and 1.0 mm; for example, it is passed with pressure through a screen in the form of a narrow-meshed metal wire gauze (10×10 up to 30×30 mesh per $cm^2$).

This dried egg yolk powder (A) is subsequently subjected to an extraction process (b) using a fat-dissolving extractant, which should be affected over a period of three to seven days, but preferably four to five days. Suitable extractants are preferably aliphatic alcohols (having one to five, preferably having one to four, carbon atoms per molecule, expediently methanol or ethanol) and/or aliphatic ketones (having up to five carbon atoms per molecule, expediently acetone), and/or Freons, and/or aliphatic ethers (having up to seven carbon atoms per molecule, in particular dialkyl ethers, such as diethyl ether, and cyclic ethers, in particular tetrahydrofuran), and/or aliphatic esters, preferably ethyl acetate, and/or, alternatively, carbon dioxide.

The extraction technique used can be selected from a range of conventional laboratory techniques, but, alternatively, a combination of a plurality of the methods listed hereinbelow may also be used:

maceration under pressures which can be either lower or moderately higher than atmospheric pressure, and/or extraction by the Soxhlet method, and/or extraction under pressure using carbon dioxide, and/or refluxing under mild conditions.

After the extraction treatment, the extractant used is slowly distilled off in step (c), a viscous residue (B) remaining, which is used as starting material for the subsequent process steps. Subsequently, this viscous residue (B) is aged in two steps (d and e), first at ambient temperature over a period of up to 10 hours, preferably for five to seven hours and subsequently at a temperature from 7° to 12° C. over a period of up to 24 hours, until a distinctly detectable phase separation takes place. The less viscous phase (C) formed during the ageing process is separated off in step (f), for example either by decanting off or with the aid of a separator, and centrifuged over a period of 20 to 40 minutes, preferably for 30 minutes, at a speed of up to 7,000 revolutions per minute, for example at a speed of 900 to 1,200 revolutions per minute, preferably from 4,000 to 7,000 revolutions per minute.

This results in phase separation, whereupon the less viscous phase (D) formed is separated off, for example by decanting off or with the aid of a separator, and further processed. The more viscous phase is discarded.

The less viscous phase (D) obtained is then mixed, in step (h), with demineralized water, a ratio of between 1:2 and 1:5 by volume being selected. The mixture obtained is then heated over a period of 30 to 90 minutes, preferably for 60 minutes, at a temperature of 90° to 120° C., preferably 95° to 100° C. After the mixture has cooled to ambient temperature, phase separation takes place, whereupon the less viscous component (E) is separated off, for example by decanting off and/or with the aid of a separating funnel (step (i)). The more viscous component is discarded.

In step (j), the less viscous component (E) obtained is centrifuged at a speed of up to 7,000 revolutions per minute, for example a speed of 900 to 1,200 revolutions per minute, preferably 4,000 to 7,000 revolutions per minute, over a period of between 20 and 40 minutes, preferably 30 minutes, which, again, results in phase separation. The less viscous component (F) is, for example, decanted off or separated off by means of a separator. The more viscous phase is discarded.

In step (k), the less viscous component (F) is held over a period of not more than 24 hours at a temperature of 7° to 12° C. until a distinct phase separation takes place again. The less viscous phase (G) is separated off, for example by decanting, and the more viscous phase formed is discarded. The less viscous phase (G) is centrifuged over a period of between 20 and 40 minutes, preferably for 30 minutes, at a speed of up to 7,000 revolutions per minute, for example a speed of 900 to 1,200 revolutions per minute, preferably 4,000 to 7,000 revolutions per minute (step (l)). The less viscous phase formed (H) is the end product.

If appropriate, the process steps may also be repeated, either starting with mixing (D) with demineralized water up to the centrifugation of (G) (steps (h) to (l)), or starting with the centrifugation of (E) up to the centrifugation of (G) (steps (j) to (l)), to obtain a particularly pure end product (H) of the present invention.

The end product (H) is a fluid oil, yellow to reddish in colour, depending on the starting material used, and can be stored without added preservatives.

The present invention is now illustrated in greater detail with the aid of a representative example.

EXAMPLE 1

(a) The egg yolk of 10 fresh chicken eggs was dried at a temperature of 60° C. using a laboratory drying oven. The dried egg yolk was then passed with pressure through a commercially available, hemispherical stainless-steel household sieve (20×20 mesh per cm$^2$) and so comminuted to a mean particle size of approximately 0.5 mm.

(b) This dried egg yolk powder was subsequently subjected to a five-day extraction treatment in a typical laboratory Soxhlet apparatus using 250 ml of analytical-grade acetone.

(c) After the extraction treatment, the acetone used was distilled off under slightly subatmospheric pressure using a rotary evaporator.

(d)+ (e) This gave a viscous residue, which was subsequently aged for six hours at ambient temperature and then for 24 hours in a thermostatically controlled cool room at 10° C. Towards the end of the ageing process, distinct phase separation was observed.

(f) The less viscous phase was thereupon decanted off, and the more viscous phase discarded.

(g) The less viscous component was then centrifuged over a period of 30 minutes at a speed of 1,100 revolutions per minute. This resulted in phase separation, whereupon the less viscous phase formed was decanted off and the more viscous phase discarded.

(h)+ (i) The less viscous phase obtained was then treated with demineralized water at a ratio of 1:4 by volume. This mixture was heated over a period of 60 minutes at a temperature of 96° C. After the mixture had cooled to ambient temperature, phase separation took place, whereupon the less viscous component was separated off by decanting. The more viscous component was discarded.

(j) The less viscous component obtained was centrifuged at a speed of 1,100 revolutions per minute over a period of 30 minutes, which resulted in phase separation. The more viscous phase was discarded.

(k) The less viscous component which had been decanted off was held for a period of 24 hours in a thermostatically controlled cool room at a temperature of 10° C., during which process distinct phase separation took place. The more viscous phase formed was discarded and the less viscous phase decanted off.

(l) The less viscous phase was subsequently centrifuged over a period of 30 minutes at a speed of 1,100 revolutions per minute. The less viscous phase formed in this process was the end product of the present invention, a yellowish, highly fluid oil which was stable upon storage without added preservatives.

EXAMPLE 2

The process sequence of Example 1 was repeated using the egg yolk of 10 fresh chicken eggs, but the centrifuging in process steps (g), (j) and (l) was carried out at a speed of 6,000 revolutions per minute.

I claim:

1. A process for obtaining ultrapure egg oil from avian or reptilian egg yolk, comprising the steps of:

a) drying the egg yolk at temperatures up to 90° C. and comminuting the dried egg yolk to give a pulverulent product (A), b) extracting the product (A) obtained in step (a) over a period of three to seven days using a fat-dissolving extractant, c) distilling off the extractant to obtain a viscous residue (B), d) aging the residue (B) obtained in step (c) at ambient temperature over a period of up to 10 hours, e) further aging the residue (B) at a temperature of between 7° and 12° C. over a period of up to 24 hours until distinct phase separation takes place, f) separating off a less viscous phase (C) formed upon phase separation in step (e), g) centrifuging the less viscous phase (C) obtained in step (f) for 20 to 40 minutes at a speed of up to 7000 revolutions per minute, and separating off a less viscous phase (D), h) mixing the phase (D) obtained in step (g) with demineralized water in a ratio of 1:2 to 1:5 by volume, and heating the mixture over a period of 30 to 90 minutes at a temperature of 90° to 120° C., i) cooling the aqueous mixture obtained in step (h) to ambient temperature and separating off a less viscous phase (E), j) centrifuging the phase (E) obtained in step (i) for 20 to 40 minutes at a speed of up to 7000 revolutions per minute and separating off the less viscous phase (F), k) holding the phase (F) obtained in step (j) at temperatures from 7° to 12° C. over a period of up to 24 hours until distinct phase separation takes place, and separating off a less viscous phase (G), l) centrifuging the phase (G) obtained in step (k) for 20 to 40 minutes at a speed of up to 7000 revolutions per minute, and separating off the less viscous phase (H).

2. A process as claimed in claim 1, wherein the egg yolk is dried at a temperature of between 50° C. and 70° C.

3. A process as claimed in claim 1, wherein the aging in step (d) is carried out for five to seven hours.

4. A process as claimed in claim 1, wherein the heating in step (h) is carried out at a temperature of 95° to 100° C.

5. A process as claimed in claim 1, wherein the steps (h) to (l) are repeated with phase (H), obtained in step (1), in place of phase (D).

6. A process as claimed in claim 1, wherein the steps (j) to (l) are repeated with phase (H) obtained.

7. A process according to claim 1, wherein the extractant used for the extraction of product (A) in step (b) is selected from the group consisting of:

aa) aliphatic alcohols having one to five carbon atoms per molecule, bb) aliphatic ketones having up to five carbon atoms per molecule, cc) Freons, dd) aliphatic ethers having up to seven carbon atoms per molecule, ee) aliphatic esters, and ff) $CO_2$.

8. A process according to claim 7, wherein the extractant used is an aliphatic alcohol having one to four carbon atoms per molecule.

9. A process according to claim 8, wherein the extractant used is methanol or ethanol.

10. A process according to claim 7, wherein the extractant used is acetone or ethyl acetate.

11. A process according to claim 7, wherein the extractant used is a dialkyl ether.

12. A process according to claim 11, wherein the extractant used is diethyl ether.

13. A process according to claim 7, wherein the extractant used is a cyclic ether.

14. A process according to claim 1, wherein the extractant used is tetrahydrofuran.

15. A process according to claim 1, wherein the step of extraction of product (A) in step (b) is carried out under at least one of the conditions of a1) to d1):

a1) maceration under pressures between a vacuum and superatmospheric pressure, at room temperature or above b1) extraction by the Soxhlet process, c1) extraction under pressure using $CO_2$, d1) refluxing.

16. A process according to claim 1, wherein the extraction of product (A) in step (b) is carried out over a period of from four to five days.

17. A process according to claim 1, wherein separating off of phases (C) to (H), is effected by one of the steps of decanting or using a separator.

18. A process according to claim 1, wherein the centrifuging of phases (C), (E) and (G) in each of steps (g), (j) and (l) is carried out over a period of 30 minutes in each of said steps (g), (j) and (l).

19. A process according to claim 1, wherein the centrifuging of phase (C) in step (g), of phase (E) in step (j) and of phase (G) in step (l) is carried out at a speed of 4000 to 7000 revolutions per minute.

20. A process according to claim 1, wherein the centrifuging of phase (C) in step (g), of phase (E) in step (j) and of phase (G) in step (l) is carried out at a speed of 900 to 1200 revolutions per minute.

21. A process according to claim 1, wherein the mixture of phase (D), and demineralized water, which is prepared in step (h), is heated for 60 minutes.

22. A process for treating skin burns comprising applying to the skin area damaged by the burn an effective amount of the ultrapure egg oil produced by the method of claim 1.

23. A process for treating the skin for cosmetic purposes comprising applying to the desired skin area an effective amount of the ultrapure egg oil produced by the method of claim 1.

* * * * *